US007657326B2

(12) United States Patent
Bodner et al.

(10) Patent No.: US 7,657,326 B2
(45) Date of Patent: Feb. 2, 2010

(54) CARDIAC LEAD WITH A RETRACTABLE HELIX

(75) Inventors: Jeffrey P. Bodner, St. Paul, MN (US); Walter C. Laroche, Crystal, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 271 days.

(21) Appl. No.: 11/557,815

(22) Filed: Nov. 8, 2006

(65) Prior Publication Data

US 2008/0109042 A1    May 8, 2008

(51) Int. Cl.
*A61N 1/05* (2006.01)
(52) U.S. Cl. .................................................... 607/127
(58) Field of Classification Search ................ 607/127
See application file for complete search history.

(56) References Cited

U.S. PATENT DOCUMENTS

| 4,233,992 | A | * | 11/1980 | Bisping | 607/127 |
|---|---|---|---|---|---|
| 4,282,885 | A | * | 8/1981 | Bisping | 607/127 |
| 4,886,074 | A | | 12/1989 | Bisping | |
| 5,003,992 | A | | 4/1991 | Holleman et al. | |
| 5,076,285 | A | * | 12/1991 | Hess et al. | 607/127 |
| 5,129,404 | A | | 7/1992 | Spehr et al. | |
| 5,259,395 | A | * | 11/1993 | Li | 607/131 |
| 5,447,533 | A | | 9/1995 | Vachon et al. | |
| 5,575,814 | A | * | 11/1996 | Giele et al. | 607/127 |
| 5,964,795 | A | * | 10/1999 | McVenes et al. | 607/122 |
| 6,086,582 | A | * | 7/2000 | Altman et al. | 606/41 |
| 6,152,954 | A | | 11/2000 | Scheiner et al. | |
| 6,212,434 | B1 | | 4/2001 | Scheiner et al. | |
| 6,256,541 | B1 | * | 7/2001 | Heil et al. | 607/123 |
| 6,296,630 | B1 | * | 10/2001 | Altman et al. | 604/508 |
| 6,463,334 | B1 | | 10/2002 | Flynn et al. | |
| 6,687,550 | B1 | | 2/2004 | Doan | |
| 6,819,959 | B1 | | 11/2004 | Doan et al. | |
| 6,931,286 | B2 | | 8/2005 | Sigg et al. | |
| 7,158,838 | B2 | | 1/2007 | Seifert et al. | |
| 2004/0059404 | A1 | | 3/2004 | Bjorklund et al. | |
| 2004/0068299 | A1 | | 4/2004 | Laske et al. | |
| 2004/0147963 | A1 | * | 7/2004 | Sommer et al. | 607/3 |
| 2005/0070984 | A1 | | 3/2005 | Sundberg | |
| 2007/0156218 | A1 | | 7/2007 | Williams | |

FOREIGN PATENT DOCUMENTS

WO     2004028348     4/2004

OTHER PUBLICATIONS

International Search Report and Written Opinion of international application No. PCT/US2007/077528, mailed Feb. 2, 2008, 13 pp.

* cited by examiner

*Primary Examiner*—Carl H Layno
*Assistant Examiner*—Jeremiah T Kimball
(74) *Attorney, Agent, or Firm*—Faegre & Benson LLP (57) ABSTRACT

A cardiac rhythm management system for securing a cardiac lead within a patient's heart is provided. According to the present invention, the cardiac rhythm management system includes a fixation helix for securing and stabilizing the lead at a target location in a patient's heart. The fixation helix is adapted to extend from a first position disposed over the electrode to a second position located distally to the distal end of the cardiac lead.

21 Claims, 12 Drawing Sheets

CARDIAC LEAD WITH A RETRACTABLE HELIX

TECHNICAL FIELD

The present invention relates to the field of medical leads. More specifically, the present invention is directed to a medical electrical lead having an extendable and retractable helix for securing the distal end of the cardiac lead within a cardiac chamber.

BACKGROUND

Implantable medical devices for treating irregular contractions of the heart with electrical stimuli are well known. Exemplary implantable devices are defibrillators and pacemakers. Various types of electrical leads for defibrillators and pacemakers have been suggested, many of which are placed transvenously. Such leads are introduced into the patient's vasculature at a venous access site and travel through veins to the sites where the leads' electrodes will be implanted or otherwise contact target coronary tissue. Electrodes for transvenously-placed leads can be implanted in the myocardium of the right atrium or ventricle, or alternatively, another location within the coronary venous system.

Various techniques have been used to facilitate fixation of the foregoing types of leads at the desired implantation sites. For leads implanted within a cardiac chamber, fixation techniques should provide fixation stable enough to withstand natural heart motion and retrograde blood flow which tend to push the lead out of the location into which the electrode is implanted. Additionally, it is desirable to permit and facilitate repositioning or removal of the lead and fixation structures after implantation if necessary or desired.

Internal helixes for fixing leads are known in the art. It is also recognized that the larger the helix is in diameter, the more stable fixation it provides. In a typical lead configuration, a fixation helix is extended and retracted from a position located internally within the lead body or catheter. As such, the size of the fixation helix used to secure lead bodies is limited by the diameter of the lead body or catheter. The size and type of electrode that is placed within the lead is also limited by this configuration.

Accordingly, there is a continuing need for improved devices and methods for fixation of cardiac leads in the coronary system. In particular, there is a need in the art for a fixation approach that effectively secures and stabilizes the lead electrodes in the target coronary location while still permitting subsequent removal of the lead.

SUMMARY

The present invention, according to one embodiment, is a cardiac rhythm management system including a pulse generator adapted to deliver a therapy to a patient's heart, and an electrical lead, including an electrical lead body and proximal and distal portions. The proximal portion is operatively coupled to the pulse generator and the distal portion is disposed in a heart chamber. The cardiac rhythm management system also includes at least one electrode located at the distal end of the electrical lead and a fixation helix adapted to extend from a first position disposed over the distal portion of the electrical lead including the electrode to a second position located distally to the distal end of the electrical lead. In another embodiment of the present invention, the cardiac rhythm management system further includes an actuation mechanism adapted to manipulate the fixation helix from the first position to the second position.

According to another embodiment of the present invention, a lead includes a proximal portion and a distal portion, the proximal portion adapted to be coupled to a pulse generator and the distal portion disposed in a chamber of the heart; a fixation helix having a proximal end and a distal end, the fixation helix movably coupled to the electrical lead; and at least one electrode located at a distal end of the electrical lead. The electrode is disposed within the fixation helix and adapted to move from a distal position to a proximal position located within the fixation helix.

According to yet another embodiment of the present invention a lead for placement at a site located within a chamber of a heart includes an electrical lead body having a proximal portion and a distal portion; at least one electrode; and a fixation means disposed over the electrode for securing the distal end of the lead in the heart chamber.

According to yet another embodiment of the present invention, a cardiac rhythm management system includes: a pulse generator adapted to deliver a therapy to a patient's heart; an electrical lead having a lead body including a proximal portion and a distal portion, the distal portion disposed in a chamber of the heart; at least one electrode located at a distal end of the electrical lead; and a fixation helix disposed over the distal portion of the lead including the electrode. The fixation helix is configured so as not to snag tissue during insertion of the lead into a patient's vasculature.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

As shown in FIG. 2A, a fixation helix is retracted over the distal end the lead.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
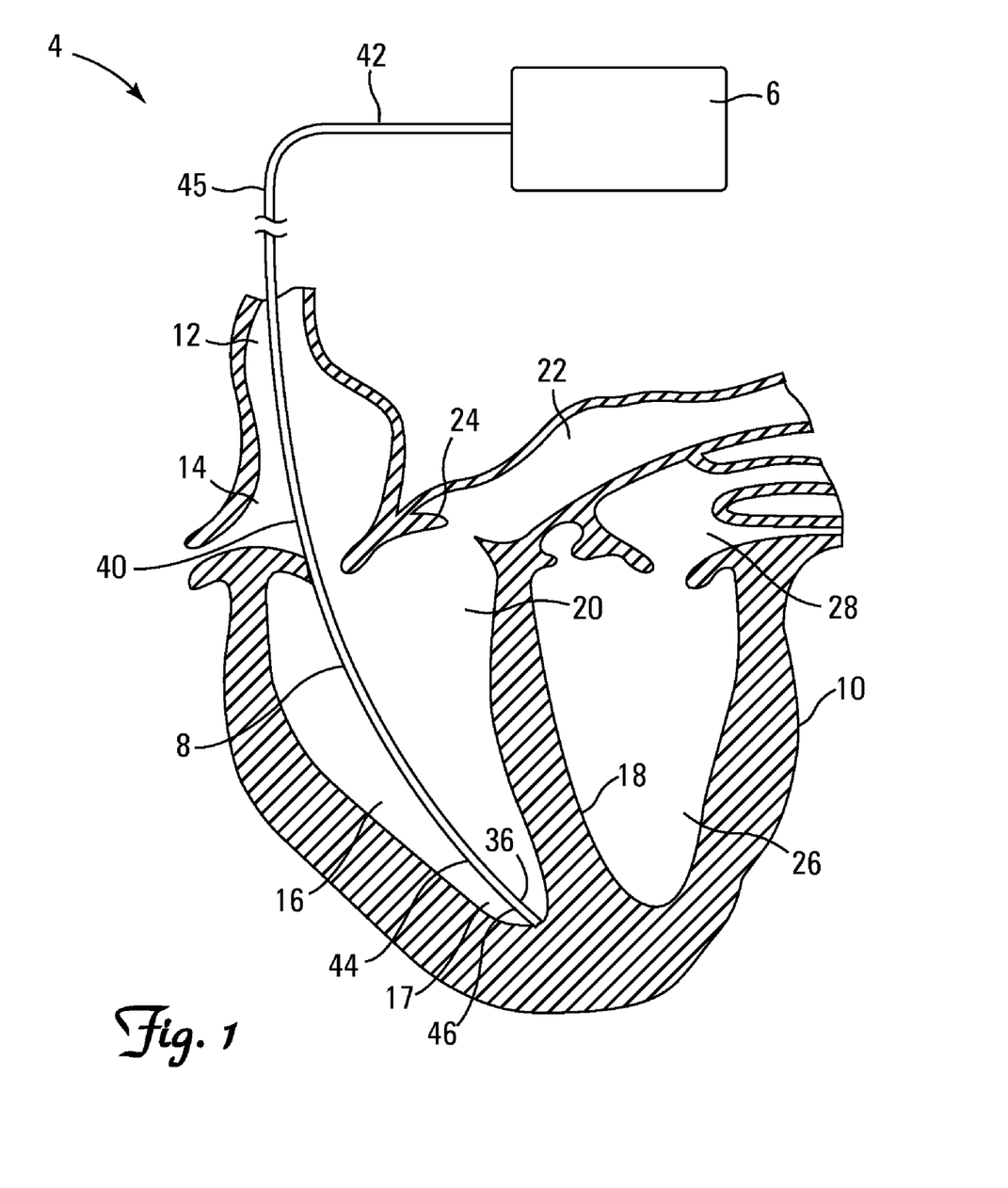
FIG. 1 is a perspective view of a pulse generator coupled to a lead deployed in a patient's heart according to one embodiment of the present invention.

FIG. 1 shows a cardiac rhythm management system 4 in accordance with the present invention. The cardiac rhythm management system 4 includes a pulse generator 6 coupled to an electrical lead 8 deployed in a patient's heart 10. As shown in FIG. 1, the heart 10 includes a superior vena cava 12, a right atrium 14, a right ventricle 16 having an apex 17, a ventricular septum 18, a ventricular outflow tract 20, which leads to a pulmonary artery 22 having a pulmonary valve 24, a left ventricle 26, and a left atrium 28. In one embodiment, the lead 8 is adapted to deliver an electrical pulse, such as a pacing or defibrillation pulse, to the heart 10 via an electrode 36 positioned in the right ventricle 16 near the right ventricular apex 17.

The lead 8 includes an elongate, flexible lead body 40 having a proximal portion 42 and a distal portion 44. The lead 8 also includes one or more conductors, such as a coiled conductor, for conducting energy from the pulse generator 6 to the heart 10, and also to receive signals from the heart 10. Additionally, the lead 8 may have a co-radial design including multiple conductor coils. The lead 8 further includes outer insulation 45 to insulate the conductor. The conductor or conductors are coupled to one or more electrodes, such as electrode 36. In one embodiment of the present invention, the lead 8 includes a lumen for receiving a guiding element such as a guide wire or a stylet.

The proximal portion 42 is operatively coupled to the pulse generator 6. Additionally, the proximal portion 42 is operable to manipulate the distal portion 44 of the lead 8 through the vasculature to position the distal end 46 of the lead 8 including the electrode 36 into a target location within a heart chamber using techniques well known in the art. It is appreciated that the lead 8 can be deployed to alternate locations within the heart such as the left side of the heart as is known in the art (e.g. the left ventricle).

In one embodiment of the present invention, the distal portion 44 is guided through the superior vena cava 12 and the right atrium 14 to a target position located near the right ventricular apex 17 of the heart 10. The distal portion 44 of the lead 8 includes at least one electrode 36 at the distal end 46 of the lead body 40. The distal end 46 of the lead 8 is secured to the myocardium using a fixation device. According to an embodiment of the present invention, the fixation device is a fixation helix that extends and retracts over a distal portion 44 of the lead body 40 including the electrode 36 located at a distal end 46 of the lead 8.

FIGS. 2A-2D show multiple views of the distal portion 44 of the lead 8 in accordance with the present invention. The distal portion 44 of the lead 8 includes a distal end region 60 including a distal assembly 71, a distal sheath 75, an electrode 80, and a fixation helix 82. The electrode 80 is located within the distal sheath 75 and includes an electrode tip 84. The fixation helix 82 is coupled to the distal assembly 71, and is disposed over the distal sheath 75 and the electrode 80. According to a further embodiment of the present invention the fixation helix 82 is rotatably disposed over the sheath 75.

Figure 2A:
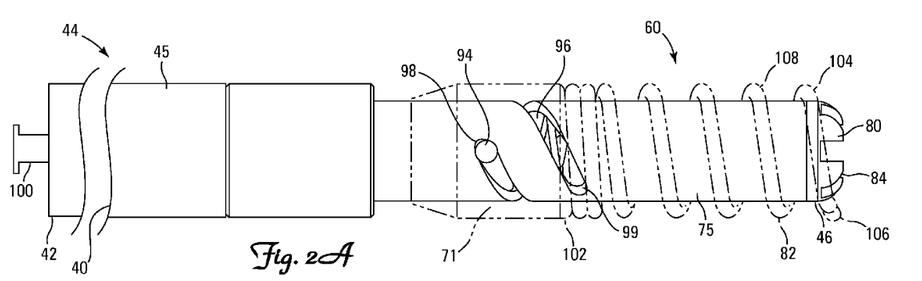
FIG. 2A is a side plan view and FIG. 2B is a sectional view of a distal portion of the lead shown in FIG. 1.
Figure 2B:
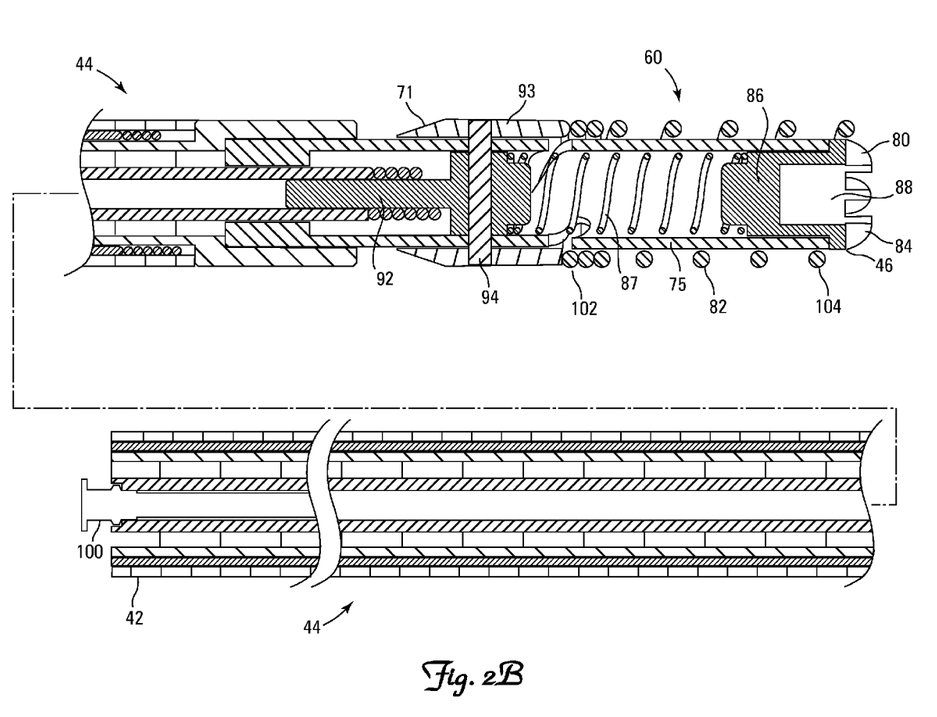
Figure 2C:
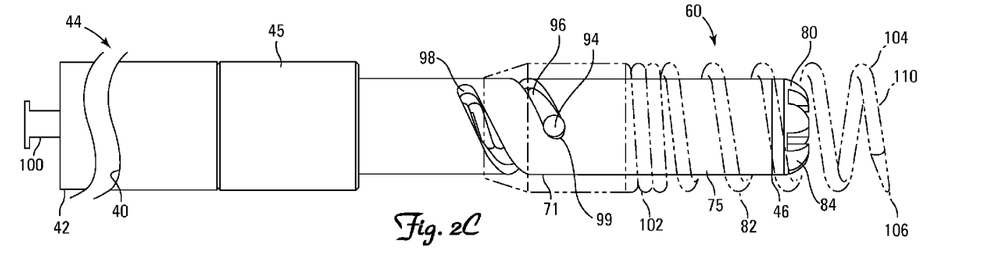
FIG. 2C is side plan view and FIG. 2D is a sectional view of the distal portion shown in FIG. 1. As shown, the fixation helix extends over the distal end of the lead.
Figure 2D:
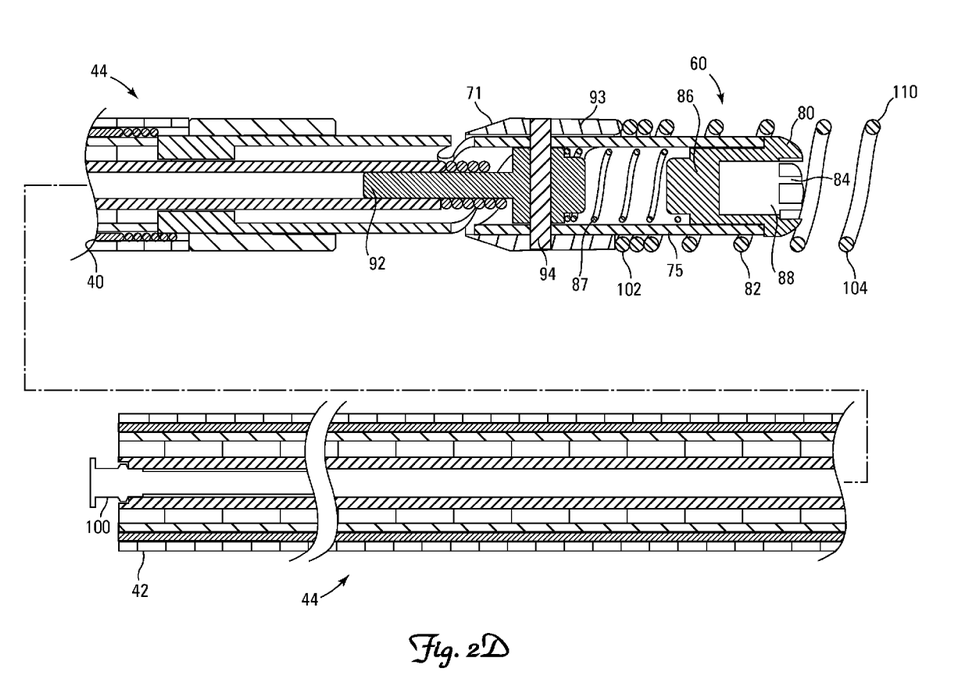

As illustrated in FIGS. 2B and 2D, the electrode 80 is disposed within the distal sheath 75 and is located at a distal end 46 of the lead body 40. The electrode 80 is in electrical communication with the distal end 46 of the lead 8 through a conductor 86 deposited axially along an inner surface of the distal sheath 75. The conductor 86 communicates with the conductor coil in the lead body 40 through a secondary conductor coil 87 located in the distal portion 44 of the lead 8. In one embodiment, the outer surface of the distal sheath 75 is coated with a nonconductive material such as is known in the art (e.g. paralyene). This prevents electrical noise or "chatter" from interfering with the electrical pulse produced by the electrode 80. The electrode 80 can have any configuration as is known in the art. According to one embodiment, the electrode 80 has a generally hemispherical configuration. According to another embodiment, the electrode 80 is a slotted tip electrode and includes an electrode tip 84 and a reservoir 88. The reservoir 88 is adapted to hold and deliver a drug to the myocardial tissue at a target location within the heart 10. In one embodiment of the present invention, the drug is a steroid for reducing inflammation at the target location. Alternatively, the drug can be any other drug or therapeutic agent known in the art for delivering therapy to a patient's heart 10. Furthermore, it is appreciated that other medical devices such as sensors and the like can be adapted to be positioned and secured using the features of the present invention.

As best viewed in FIGS. 2B and 2D, the distal assembly 71 includes a distal shaft 92, a distal assembly housing 93, and a rotatable pin 94. The pin 94 travels in a groove 96 (best viewed in FIGS. 2A and 2C) located in the distal sheath 75. The groove 96 includes stop regions 98 and 99, and controls the advancement and rotation of the fixation helix 82. The path of the groove 96 controls the ratio of degrees of rotation of the helix 82 to the distance of extension. According to one embodiment of the present invention, the groove 96 is a helical groove. Actuation of the pin 94 within the distal assembly 71 rotates the fixation helix 82 over the distal sheath 75 and electrode 80 in a proximal or distal direction. In FIGS. 2A-2D a turn pin 100 is used to rotate the inner conductor coil, thus causing the pin 94 located within the distal assembly 71 to rotate the fixation helix 82 over the distal sheath 75 and electrode 80 in a distal direction.

The fixation helix 82 includes a proximal end 102, a distal end 104, and a tip 106. According to an embodiment of the present invention, the fixation helix 82 rotatably extends and retracts independently of the electrode 80 disposed within the distal sheath 75. The fixation helix 82 extends and retracts from a retracted position 108 (shown in FIG. 2A) to an extended position 110 (shown in FIG. 2C), and moves relative to the sheath 75. The groove 96 located in the distal sheath 75 controls the advancement of the fixation helix by providing stop regions 98 and 99 for both the extension and retraction of the helix. When a distal rotation force is applied to the distal assembly 71, the stop region 99 prevents the fixation helix from being extended beyond its intended extended position 110. Similarly, when a proximal rotational force is applied, the stop region 98 prevents the fixation helix from being retracted too far over the distal sheath 75. These features allow the fixation helix 82 to be more easily retracted and redeployed during repositioning of the lead 8 at the target location. Additionally, they allow the fixation helix 82 to be extended and retracted in a controlled manner. In one embodiment, the extended position 110 is located distally to the distal end 46 of the lead 8. In another embodiment, the extended position 110 is located distally to the electrode tip 84. In a further embodiment, the fixation helix 82 is capable of extending a distance from about 1.5 mm to about 2 mm as measured from the electrode tip 84. In yet another embodiment, when in the retracted position 108, the distal end 104 of the fixation helix 82 is radially aligned with the electrode tip 84.

According to an embodiment of the present invention, the fixation helix 82 is in the retracted position 108 when the lead 8 is guided through the vasculature and positioned at the target site. In this position, the tip 106, best viewed in FIGS. 3A and 3B discussed below, will not snag on the vascular tissue as the lead 8 is guided through the vasculature. During manufacture the tip 106 is ground such that it deflects inward towards an interior of the helix 82 (FIG. 3B). It is this configuration that allows the tip 106 not to snag on the vascular tissue as the lead 8 is guided through a patient's vasculature system. In an embodiment of the present invention, the tip 106 includes one facet. In another embodiment of the present invention, the tip 106 of the helix 82 may include two or more facets for engaging the myocardial tissue at the target location. According to alternate embodiments of the present invention, the tip 106 shape may be configured to be pyramidal, conical, blunt, rounded, or another shape as known in the art. Once the helix 82 is in the extended position 110, the tip 106, despite its inward deflection, is capable of engaging the myocardial tissue at the target location.

The present invention allows for a larger fixation helix 82 to be used to secure the lead 8 having a predetermined diameter at a target location as the fixation helix 82 is disposed over the distal portion 44 of the lead body 40. An outer catheter or guiding member provided for the purpose of protecting the helix 82 is not required as the helix tip 106 will not snag tissue in its retracted position 108. Larger helixes are more capable of withstanding the contractions of the heart and, thus, are more stable for securing leads. In one embodiment of the present invention, the outer diameter of the fixation helix 82 ranges from about 0.045 inches to about 0.092 inches. In another embodiment of the present invention, the outer diameter of the fixation helix 82 ranges from about 0.045 to about 0.050 inches. In yet another embodiment, the outer diameter of the fixation helix ranges from about 0.050 to about 0.079 inches. In yet a further embodiment, the outer diameter of the fixation helix ranges from about 0.079 to 0.092 inches.

Figure 3A:
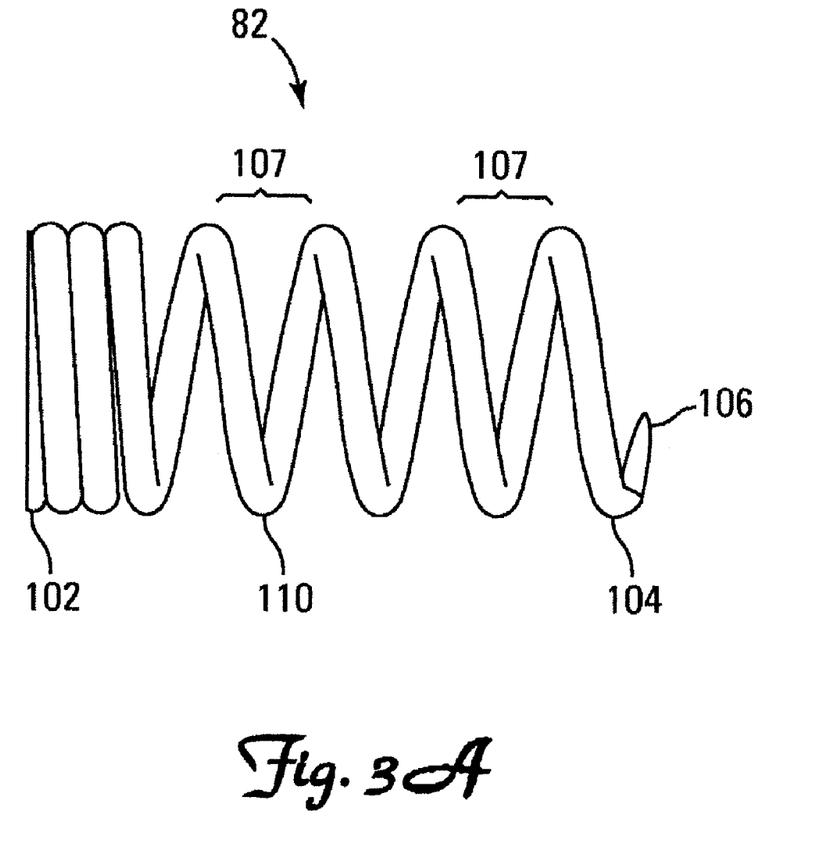
FIG. 3A is a perspective view of the fixation helix of the present invention.
Figure 3B:
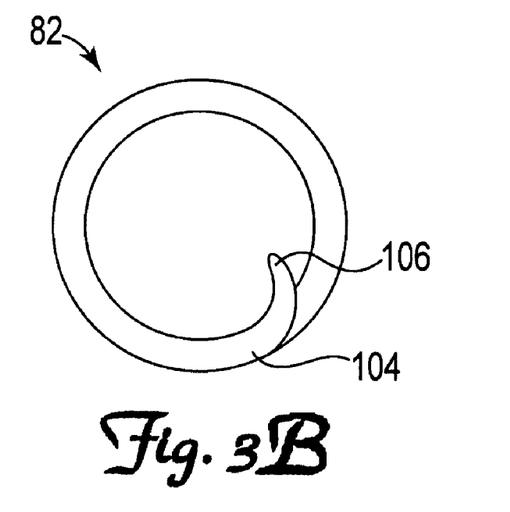
FIG. 3B is an end view of the fixation helix shown in FIG. 3A.

FIG. 3 shows the fixation helix 82 according to an embodiment of the present invention. The helix 82 includes a proximal end 102, a distal end 104, and a helix body 110 extending there between. Located at the distal end 104 is the helix tip 106. The material for forming the helix includes, but is not limited to, the following: Nitinol, NiTi alloy, titanium, spring temper 316 SS, MP35N, platinum or platinum alloy, polyurethane, bio-compatible polymers or another material as is known in the art. According to one embodiment of the present invention, the fixation helix 82 is conductive and is adapted to operate as a secondary electrode. According to another embodiment, the helix 82 is a wire coil including a non-conductive outer coating. In this embodiment, the non-conductive coating coats all of the wire helix and ranges from about 4 to about 5 microinches thick. In an alternate embodiment, the coil itself is nonconductive. The turns 107 of the helix 82 maintain a constant pitch (frequency) over a specified length of the helix body 110. In the present invention the pitch ranges from about 0.030 to about 0.050 inches. Additionally a proximal end 102 of the helix 82 includes a minimum of two full turns having a more tightly wound pitch than the specified length of the helix body 110. There is a smooth transition from the tightly wound proximal end 102 of the helix 82 to the helix body 110 having a constant pitch.

When the helix 82 is in the second position, the helix tip 106 is capable of engaging the myocardial tissue at the target location. According to an embodiment of the present invention, the helix 82 rotatably engages the myocardial tissue at the target location through the actuation of the distal assembly 71 located within the distal end region 60 of the lead 8, as shown in FIGS. 2A-2D. The helix tip 106 is rotated into the myocardial tissue until it is secured and stabilized in the target location.

Figure 4:
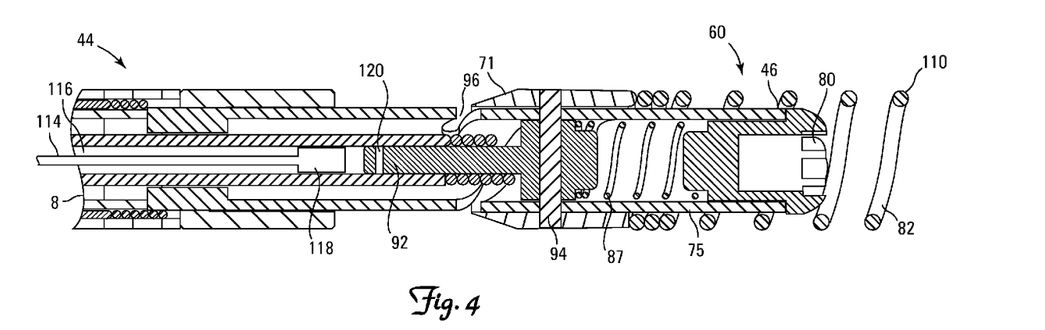
FIG. 4 is a sectional view of a stylet engaging a distal portion of a lead shown in FIGS. 2A-2D according to an embodiment of the present invention.

According to the embodiment of the present invention shown in FIG. 4, a stylet 114 is inserted into a lumen 116 provided in the lead 8. The stylet 114 is used to actuate the distal assembly 71 provided at the distal end region 60 of the lead 8. The stylet 114 includes a distal end 118 and is operated at the proximal portion 42 of the lead 8. According to one embodiment of the present invention, the distal end 118 of the stylet 114 is adapted to rotatably engage a slot 120 located on the distal shaft 92 and adapted to rotatably receive the distal end 118 of the stylet 114. When the stylet 114 is engaged in the slot 120 located on the distal shaft 92, the stylet 114 is used to rotate the distal assembly 71 thus rotating the fixation helix 82. Pushing and rotating the distal shaft 92 in a distal direction causes the pin 94 to travel through the groove 96 located in the distal sheath 75 extending the helix 82 from a retracted position 108 located over the distal portion 44 of the lead body 40 including the electrode 80 to an extended position 110 located distally the distal end 46 of the lead body 40. The helix 82 can be further rotated to engage the myocardial tissue at the target location. The stylet 114 is operated in the opposite direction to disengage the helix from the myocardial tissue and to retract the helix from the extended position 110 to its retracted position 108. The lead 8 can then be either repositioned or retrieved.

Figure 5A:
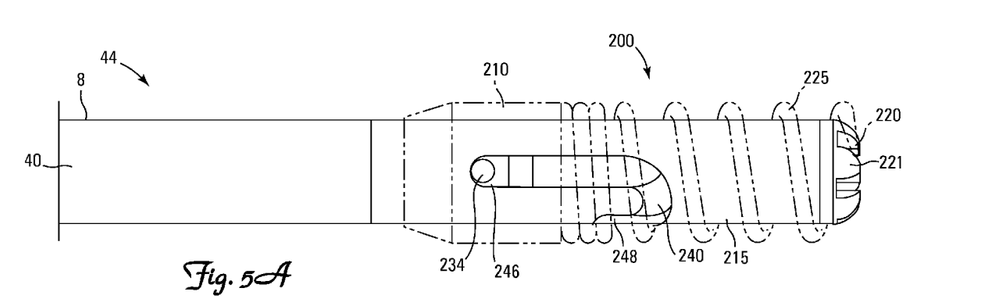
FIG. 5A is a side plan view and FIG. 5B is a sectional view of a distal portion of a lead shown in FIG. 1 according to an embodiment of the present invention.
Figure 5B:
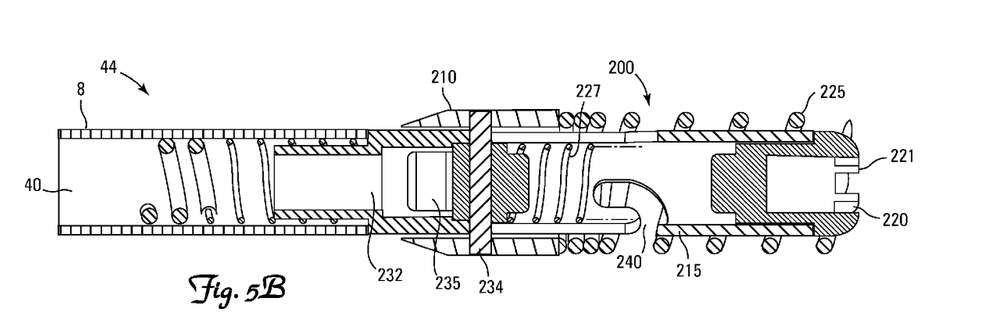
Figure 5C:
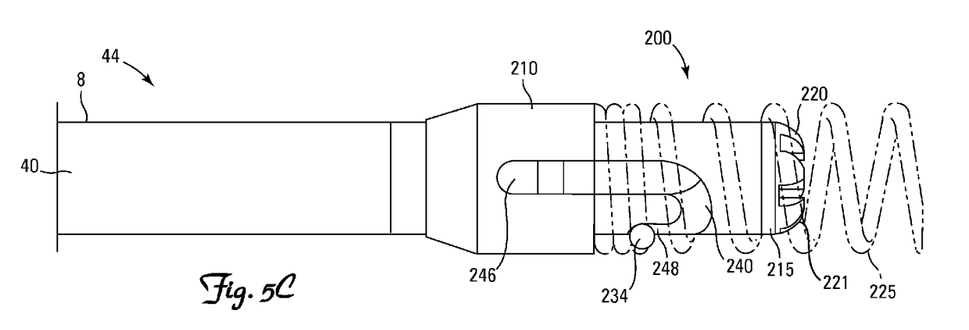
FIG. 5C is a side plan view of the distal portion illustrated in FIG. 1. As shown, the fixation helix extends over the distal portion of the lead.

In an alternate embodiment illustrated in FIGS. 5A-5C, the lead 8 includes a distal portion 200 including a distal assembly 210, a distal sheath 215, an electrode 220 including an electrode tip 221, and a fixation helix 225. The distal portion 200 also includes a spring 227 (shown in FIG. 2B). The fixation helix 225 couples with the distal assembly 210 and is disposed over the distal sheath 215 including the electrode 220. In this embodiment, as shown in FIG. 5B, the distal assembly 210 includes a distal shaft 232, a locking pin 234, and a slot 240 provided in the distal sheath 215. The locking pin 234 is slideably engaged in the slot 240. In one embodiment of the present invention, the slot 240 is a J-shaped slot. In alternative embodiments of the present invention the slot 240 can have any appropriate shape as is known in the art for slideably engaging and locking a pin 234. The locking pin 234 slides from a proximal position 246 in the J-shaped slot 240 to a distal position 248 located in the end portion of the J-shaped slot 240. The spring 227 places a tension or distal force on the pin 234 as the pin 234 moves from a proximal position 246 to a distal position 248. Additionally, the spring 227 facilitates securing the pin 234 in the curved portion of the J-shaped slot 240 by placing a distal force on the pin 234 as it is held in the distal position 248 of the J-shaped slot 240. Once the pin 234 is released from the distal position 248 of the J-shaped slot 240, the spring 227 allows the pin 234 to easily retract from a distal position 248 to a proximal position 246 within the slot 240.

Figure 6:
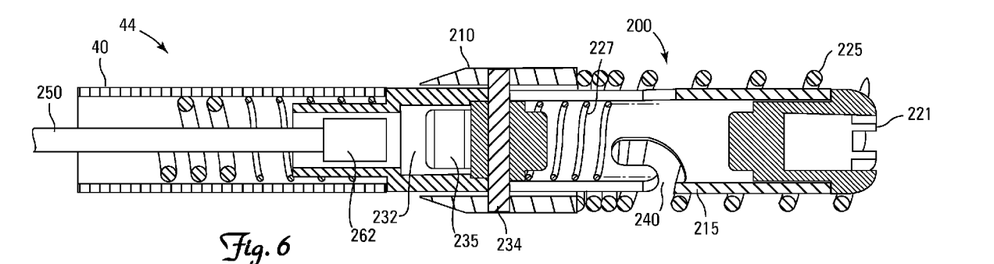
FIG. 6 is a sectional view of a stylet engaging a distal portion of a lead shown in FIGS. 5A-5C according to an embodiment of the present invention.

FIG. 6 is a sectional view of a stylet engaging a distal portion of a lead as shown in FIGS. 5A-5C. According to one embodiment of the present invention, as shown in FIG. 6, the distal shaft 232 includes a slot 235 sized to rotatably receive a flat portion of a stylet for manipulating the locking pin 234 in the J-shaped slot 240. A stylet 250 is inserted into a lumen provided in the lead 8. The stylet 250 includes a distal end 262 adapted to rotatably engage the slot 235 located on the distal shaft 232 of the distal assembly 210. A physician uses the stylet 250 to push on the locking pin 234 causing the locking pin 234 to slide from a proximal position 246 to a distal position 248 in the J-shaped slot 240 provided in a distal sheath 215. As this process occurs, the fixation helix 225 extends from a retracted position to an extended position located distally to a distal end 46 of the lead body 40. In another embodiment according to the present invention, the fixation helix 225 extends from a retracted position to an extended position located distally to the electrode tip 221. The stylet 250 is then used to lock or secure the fixation helix 225 in place by positioning the locking pin 234 in the curved portion of the J-shaped slot 240. The lead body 40, using techniques well known in the art, is then rotated in a first direction to engage and secure the fixation helix 225 in the myocardial tissue at the target site in a patient's heart.

To release the helix, the operations are reversed. The lead body 40 is rotated in a second, opposite direction to disengage the fixation helix 225 from the myocardial tissue at the target location. Then, the physician pushes forward on the stylet 250 to release the locking pin 234 from the curved portion of the J-shaped slot 240. The locking pin 234 is allowed to slide from a distal position 248 back to a proximal position 246. The lead 8 then can be repositioned at the target location or removed.

Figure 7A:
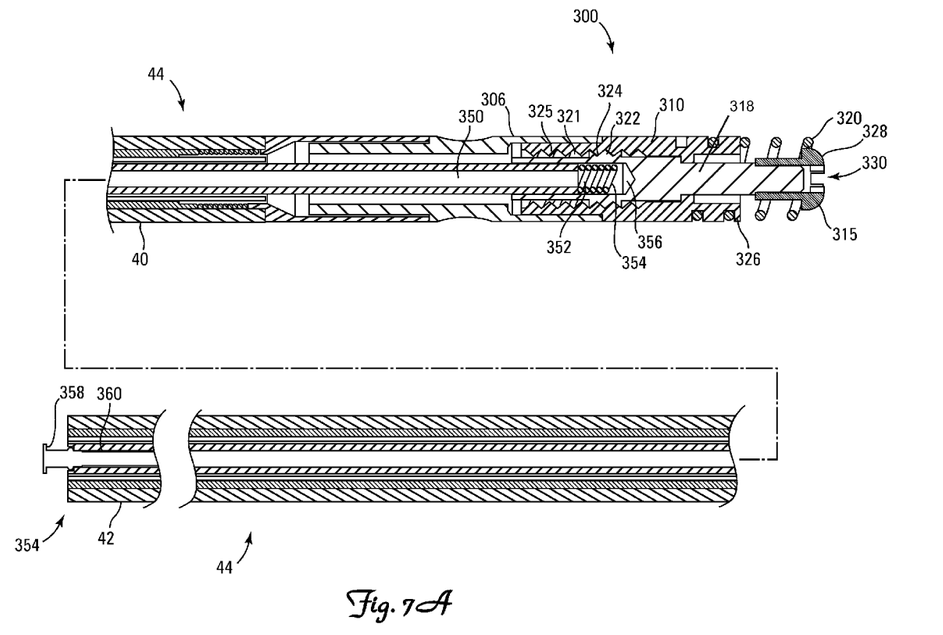
FIGS. 7A and 7B show a sectional view of a distal portion of a lead shown in FIG. 1 according to an embodiment of the present invention.
Figure 7B:
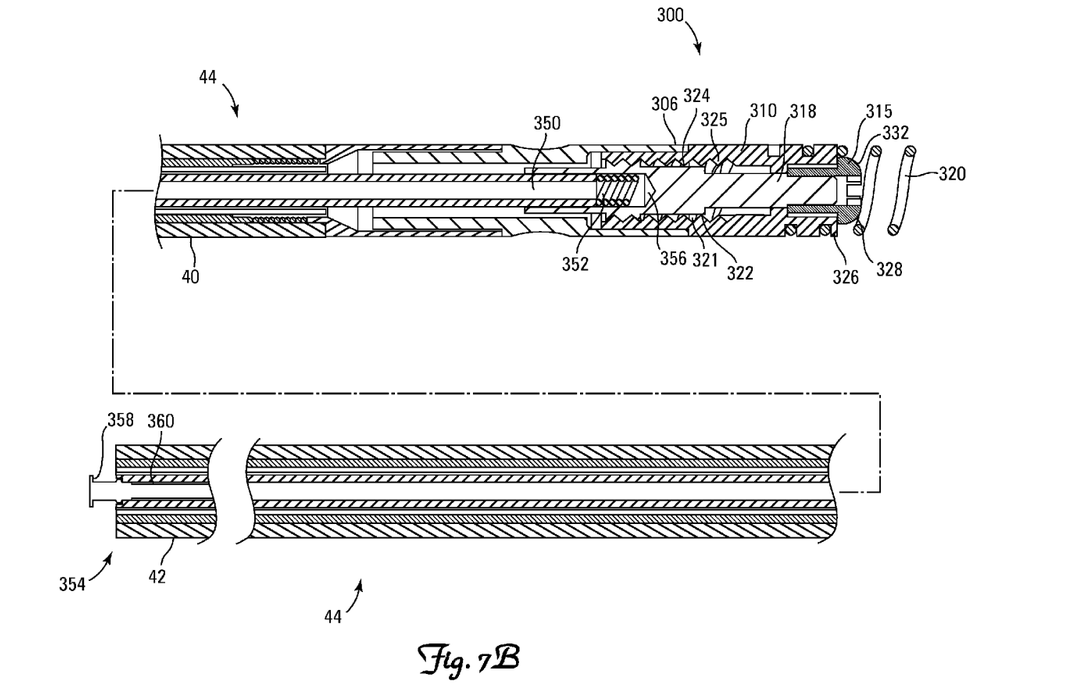

According to another embodiment of the present invention shown in FIGS. 7A and 7B, the distal portion 300 of a lead 8 includes a distal assembly 306 including a distal sheath 310, an electrode 315 disposed within the distal sheath 310, and a fixation helix 320. Additionally, the electrode 315 is coupled to a drive shaft 318 located within the distal sheath 310. The drive shaft 318 includes threads 321 on an outer portion 322 of the shaft 318 and is threadably engaged with threads 324 disposed on an inner portion 325 of the distal sheath 310. The fixation helix 320 extends over a distal end 326 of the lead body 40 to a point distal to an electrode tip 328. In this embodiment, the fixation helix 320 is stationary with respect to the distal sheath 310. The distal position 330 of the electrode tip 328 within the fixation helix 320 prevents the fixation helix 320 from snagging on any myocardial tissue during the insertion and deployment of the lead 8. After deployment of the lead 8 into a cardiac chamber, the lead body 40 is rotated using techniques well known in the art to secure and stabilize the fixation helix 320 in the myocardial tissue at the target location in a patient's heart. Then, the electrode 315 is moved within the fixation helix 320 from a distal position 330 located distally to a distal end 46 of the lead 8 to a proximal position 332. According to one embodiment of the present invention, in the distal position 330, the electrode tip 328 is in close proximity to the myocardial tissue. In another embodiment of the present invention, the electrode tip 328 contacts the myocardial tissue at the target location. The electrode position can be selected and adjusted as necessary.

According to one embodiment of the present invention, as shown in FIG. 7A-7B, the lead 8 includes a terminal drive mechanism 350 having an inner coil 352 extending the length of the lead body 40. The inner coil 352 includes a terminal end 354 adapted to rotatably engage a recess 356 provided on the drive shaft 318 located within the distal sheath 310. A terminal pin 358 is fixed to a proximal end 360 of the inner coil 352. Rotation of the terminal pin 358 turns the inner coil 352, engaging and rotating the drive shaft 318 located within the distal sheath 310. Rotation of the drive shaft 318 in a first direction moves the electrode 315 from a distal position 330 to a proximal position 332. According to one embodiment of the present invention, when the electrode 315 is in the distal position 330, the electrode 315 is in close proximity to the myocardial tissue at the target location. In alternate embodiments, the electrode 315 can contact the myocardial tissue at the target location. To remove or reposition the lead 8, the lead body 40 is rotated to disengage the fixation helix 320 from the myocardial tissue at the target location. The lead 8 can then either be repositioned or removed.

A lead including a distal portion having a fixation helix described according to the various embodiments discussed above can be deployed in a patient's heart using standard techniques known to those of skill in the art. As the helix is designed not to snag on cardiac tissue during insertion and deployment, a guide catheter or protective outer sheath is not required. This allows flexibility in determining lead and fixation helix diameter. For example, a small diameter lead may be selected having a large fixation helix disposed over an outer surface of a distal portion of the lead, optimizing fixation stability of the lead at the target location.

The fixation helix, according to the various embodiments of the present invention, allows the lead to be repositioned or removed from its target location within a patient's heart. If a clinician desires to reposition the lead, the fixation helix may be retracted from the extended position to the retracted position allowing the lead to be repositioned. The fixation helix can then be used again to secure the lead at the target location. Alternatively, the fixation helix can be retracted and the lead removed. According to another embodiment of the present invention, the fixation helix is capable of substantially permanent deployment to the target location to prevent the lead from becoming dislodged or repositioned during use.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A cardiac rhythm management system comprising:
a pulse generator adapted to deliver a therapy to a patient's heart;
an electrical lead comprising a lead body having a proximal portion and a distal portion, the proximal portion operatively coupled to the pulse generator and the distal portion adapted to be placed in a chamber of the heart, the distal portion comprising an outer surface including a recessed groove formed therein such that the groove extends at least partially through the outer surface of the distal portion of the lead body and wherein the groove includes a first stop region and a second stop region;
at least one conductor extending within the lead body;
at least one electrode located at a distal end of the electrical lead body and operatively coupled to the at least one conductor; and
a fixation helix disposed over the distal portion of the lead body including the electrode, the fixation helix adapted to extend from a retracted position disposed over the distal portion of the lead body to an extended position located distally to the distal end of the electrical lead body, the fixation helix comprising a pin slideably engaged in the groove formed in the outer surface distal portion of the lead body, wherein the pin and the groove are adapted to control the advancement of the fixation helix.

2. The cardiac rhythm management system according to claim 1, comprising an actuation mechanism adapted to extend the fixation helix from the retracted position disposed over the distal portion of the lead body to an extended position located distally to the distal end of the lead body, the actuation mechanism comprising a distal assembly including a distal shaft and a rotatable pin, wherein the fixation helix is coupled to the distal assembly.

3. The cardiac rhythm management system according to claim 1, wherein the fixation helix is adapted to retract from the extended position located distally to the distal end of the lead body to the retracted position.

4. The cardiac rhythm management system according to claim 1, wherein the fixation helix moves independently of the electrode.

5. The cardiac rhythm management system according to claim 4, wherein the fixation helix is non-conductive.

6. The cardiac rhythm management system according to claim 4, wherein the fixation helix is adapted to operate as a secondary electrode.

7. The cardiac rhythm management system according to claim 1, the fixation helix comprising a tip, wherein when the fixation helix is in the retracted position the tip will not snag tissue.

8. The cardiac rhythm management system according to claim 1, wherein an outer diameter of the fixation helix ranges from about 0.045 to about 0.092 inches.

9. The cardiac rhythm management system according to claim 1, wherein an outer diameter of the fixation helix ranges from about 0.079 to about 0.092 inches.

10. The cardiac rhythm management system according to claim 1, wherein the groove is a J-shaped groove.

11. The cardiac rhythm management system according to claim 1, wherein the groove is a helical groove.

12. A lead comprising:
   a lead body comprising a proximal portion adapted to be coupled to a pulse generator and a distal portion adapted to be placed in a chamber of the heart, the distal portion comprising an outer surface having a recessed groove formed therein such that the groove extends at least partially through the outer surface of the distal portion of the lead body and wherein the groove comprises a first stop region and a second stop region;
   a fixation helix having a proximal end and a distal end, the fixation helix stationary relative to the distal portion of the electrical lead; the fixation helix comprising a pin slideably engaged in the groove formed in the distal portion of the lead body;
   at least one conductor extending within the lead body; and
   at least one electrode located at a distal end of the lead body and operatively coupled to the at least one conductor, the electrode disposed within the fixation helix and adapted to move from a distal position located within the fixation helix to a proximal position.

13. The lead according to claim 12, further comprising an actuation mechanism for moving the electrode from the distal position located within the fixation helix to the proximal position.

14. The lead according to claim 13, wherein the actuation mechanism comprises a terminal drive mechanism.

15. The lead according to claim 12, wherein an outer diameter of the fixation helix ranges from about 0.045 to about 0.092 inches.

16. A cardiac rhythm management system comprising:
   a pulse generator adapted to deliver a therapy to a patient's heart;
   an electrical lead comprising a lead body including a proximal portion and a distal portion, the proximal portion operatively coupled to the pulse generator and the distal portion adapted to be placed in a chamber of the heart, the distal portion comprising an outer surface including a recessed groove formed therein such that the groove extends at least partially through the outer surface of the distal portion of the lead body and wherein the groove includes a first stop region and a second stop region;
   at least one conductor extending within the lead body
   at least one electrode located at a distal end of the electrical lead body and operatively coupled to the at least one electrode; and
   a fixation helix disposed over the distal portion of the lead including the electrode, the fixation helix comprising a pin slideably engaged in the groove formed in the outer surface of the distal portion of the lead body, wherein the pin and the groove are adapted to control the advancement of the fixation helix and wherein the fixation helix comprises a tip deflected inward towards an interior of the fixation helix so as not to snag tissue during insertion of the lead into a patient's vasculature.

17. The cardiac rhythm management system according to claim 16, wherein the fixation helix moves relative to the distal portion of the lead body and is adapted to extend from a retracted position disposed over the distal portion to an extended position located distally to the electrode located at the distal end of the lead body.

18. The cardiac rhythm management system according to claim 16, wherein the fixation helix is stationary relative to the distal portion of the lead body and the electrode moves within the fixation helix from a distal position to a proximal position.

19. The cardiac rhythm management system according to claim 16, wherein the fixation helix is non-conductive.

20. The cardiac rhythm management system according to claim 16, wherein the fixation helix is adapted to operate as a secondary electrode.

21. The cardiac rhythm management system according to claim 16, wherein an outer diameter of the fixation helix ranges from about 0.045 to about 0.092 inches.

* * * * *